United States Patent [19]

Palsgard et al.

[11] Patent Number: 4,848,360

[45] Date of Patent: Jul. 18, 1989

[54] DEVICE FOR PREVENTING OF SNORING

[76] Inventors: Göte Palsgard, 70211 Örebro, Nygatan 28; Karl-Johan Vikterlöf, 70361 Örebro, Olaig. 36 nb.; Carl-Eric Persson, 71400 Kopparberg, Juthemmanet Löa; Nils O. Nygren, 717 00 Storå, Björkvägen 10; Torbjörn Birgning, 71400 Kopparberg, Persgården Löa, all of Sweden

[21] Appl. No.: 68,250

[22] PCT Filed: Oct. 23, 1986

[86] PCT No.: PCT/SE86/00488
§ 371 Date: Jun. 22, 1987
§ 102(e) Date: Jun. 22, 1987

[87] PCT Pub. No.: WO87/02577
PCT Pub. Date: May 7, 1987

[30] Foreign Application Priority Data

Oct. 25, 1985 [SE] Sweden ................ 8505040

[51] Int. Cl.⁴ .................................... A61B 7/00
[52] U.S. Cl. .................. 128/773; 128/419 R; 340/575
[58] Field of Search ............ 128/1 R, 132 R, 135, 128/136, 164, 419 R, 773; 340/573, 575

[56] References Cited

U.S. PATENT DOCUMENTS 3,089,130 5/1963 Wilson ........................... 340/575
3,998,209 12/1976 Macvaugh .................. 128/419 R

FOREIGN PATENT DOCUMENTS 0145160 6/1985 European Pat. Off. ........ 128/419 R

Primary Examiner—Kyle L. Howell
Assistant Examiner—Randy Citrin
Attorney, Agent, or Firm—Notaro & Michalos

[57] ABSTRACT

A device for preventing snoring of a sleeping person comprises an arrangement (5-9) for detecting snoring sounds and an apparatus (17) controlled by this arrangement and adapted to influence the person to stop snoring. The arrangement has a sound-receiving microphone (5) and at least one frequency filter (6, 8), arranged to deliver signals deriving from sounds with frequencies typical for snoring sounds in order to determine if the present sound derives from snores. The arrangement further comprises a circuit (10-14) for determining if the signals delivered by the microphone are periodically appearing at time intervals, which are typical for snores. The circuit comprises a counter (13) which is arranged to count the number of snores. The arrangement (5-14) of the device is adapted to send activating control pulses to the apparatus when the counter (13) has detected a predetermined number of successive snores with the time intervals.

11 Claims, 1 Drawing Sheet

DEVICE FOR PREVENTING OF SNORING

FIELD OF INVENTION AND PRIOR ART

This invention relates to a device for preventing snoring of a sleeping person according to the preamble of the claim 1.

It is well known that when two or more persons are going to sleep in the same room frequently the inconvenience occurs that someone of the persons produces snoring sounds and as a consequence thereof either obstructs the falling asleep of the other or wakes up the other. This problem is probably most common among two persons who are living together and sleeping in the same bed, but can also be rather severe under other circumstances, for example in hospitals. In the latter case it may be impossible for a bedridden patient to bring the snorer to stop the snoring without waking up all the others in the ward. In some cases the problem can be so great that two persons living together choose to sleep in separate rooms, in spite of the several drawbacks this will result in. Therefore it is very desirable to be able to apply a device which prevents snoring of a sleeping person and in doing so preferably does not wake him or other persons sleeping in the same room. A device for this purpose is the object of this application.

A device of this kind is described in the Swedish patent application No. 8204375-3. This device comprises an apparatus in the form of two electrodes intended to be brought in touch with the sleeping and possibly snoring person, e.g. by putting them as a bracelet around his wrist. The electrodes are fed with a voltage, and do accordingly give the person in question a small electrical shock as soon as the sound with a frequency which is characteristic for snores is registered by a microphone included in the device. Through said electrical shock the snoring person is influenced to either change his sleeping position, so that the snoring disappears (the delivering of electrical shocks will not end before this happens), or to wake up.

This device has drawbacks which the present invention strives to reduce considerably. In the first place it is very unfortunate for the sleeping person to get an electrical shock in the same moment that a sound with a frequency similar to that of a snoring sound is propagated in the bedroom. In the second place it is quite possible that this sound does not even derive from him, but is a background sound. But if it nevertheless is originating from said person, it is possible that he has talked in his sleep or produced a single snoring or snuffling or the like. In all the cases it is unnecessary to influence the person to change his sleeping position and/or wake up, since it is not sure at all that he disturbs or can be expected to disturb anyone else in the room. It is true that the snoring of a person in question is prevented by this device, but the probability of unnecessarily disturbing this person is very high.

The object of the present invention is to provide a device of the above-mentioned kind, which influences a sleeping person solely if he snores continously during a rather long time interval and so that he stops snoring, at the same time as the device prevents such an influence when the sounds registered by the microphone are not originating from snores.

SUMMARY OF THE INVENTION

In accordance with the invention this object is obtained by providing the device with the characteristics of claim 1.

The advantages of the device according to the invention are achieved through the understanding that snores appear periodically at typical time intervals, and that the device is provided with means, which test if a detected sound has this periodicity and which are arranged to control the arrangement to influence the snorer solely if he has produced a predetermined number of successive snores with said time intervals.

As a result of this, background noises and isolated snores cannot cause unnecessary influences on or disturbences of the sleeping person, but he is only influenced when he is really snoring during a prolonged period of time, e.g. 30 seconds. Not until the snoring is proceeding over a certain period of time it will have a disturbing influence upon the people in the surroundings. Naturally, a person that has not yet fallen asleep or a sleeping person is hardly disturbed by one single snore in his trying to sleep. Thus, the advantages with respect to the device already known are apparent.

BRIEF DESCRIPTION OF THE DRAWING

With reference to the appended drawing, below follows a specific description of a preferred embodiment of the device according to the invention described as an example.

In the drawings.

DETAILED DESCRIPTION OF A PREFERRED EMBODIMENT

Figure 1:
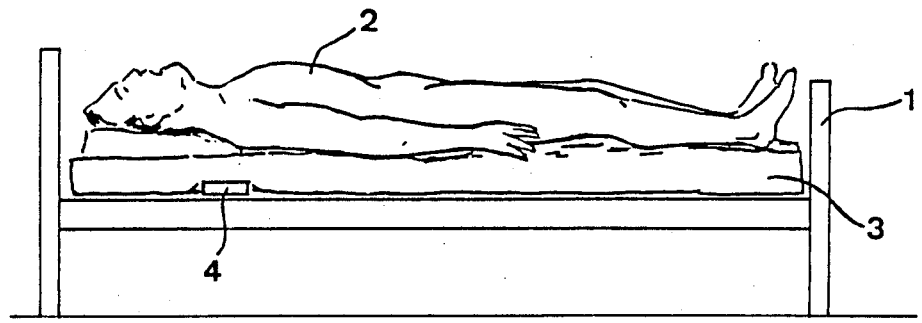
FIG. 1 is a schematic view of a sleeping person with the device according to the invention localized under the bed mattress.

In FIG. 1 there is shown a sleeping person 2 lying on a bed 1. A box 4 is located under the bed mattress 3 at the level of the head of the person. The complete device according to the invention except for an electricity source and its wires for the connection with the components in the box is disposed in this box. The elements being located outside the box are without importance for the invention and are accordingly not shown in the figures. It is also possible to arrange the power supply by means of one or more batteries, which in such a case can be disposed inside the box and by that enable a simple application and moving of the device according to the invention.

Figure 2:
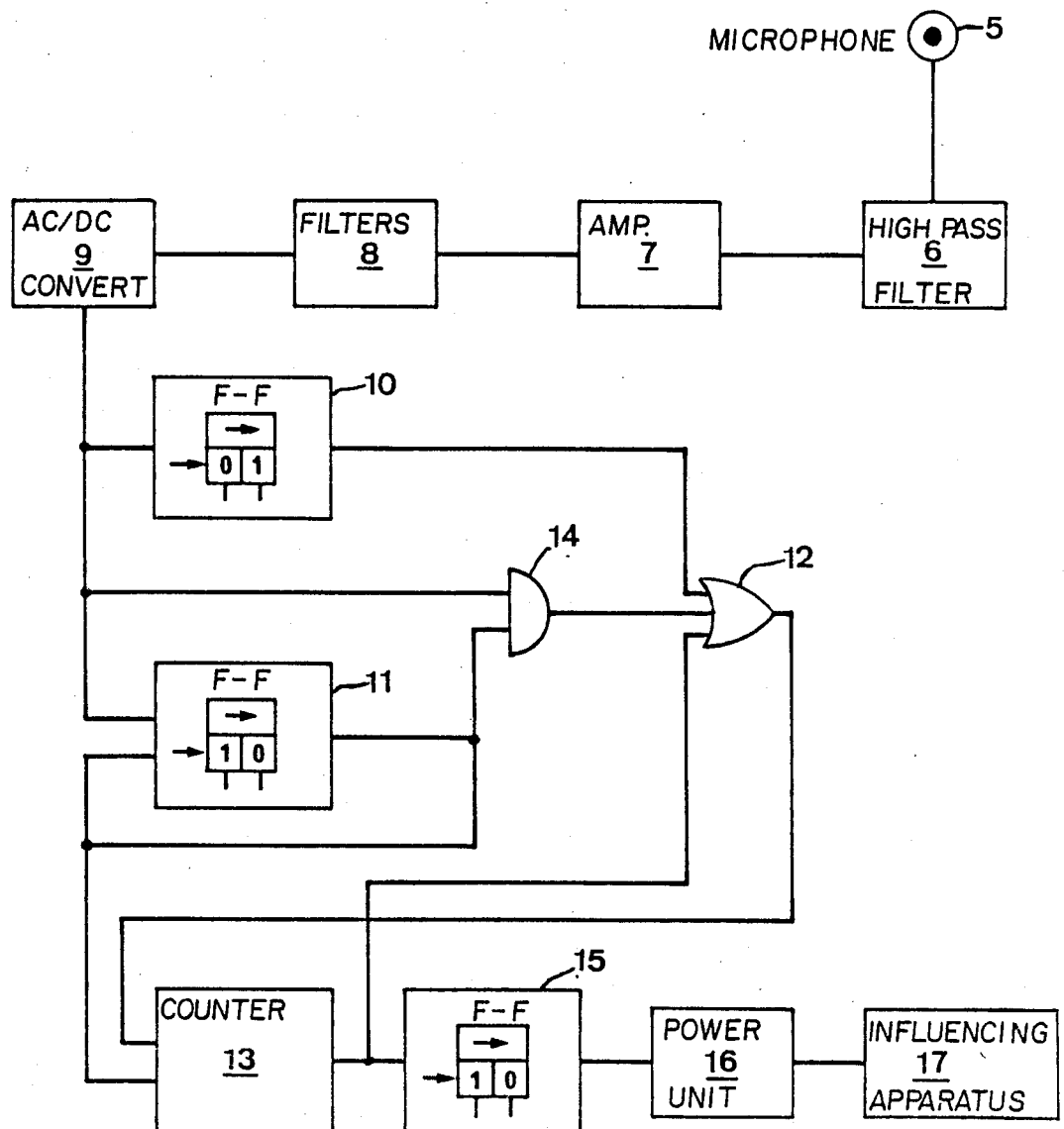
FIG. 2 is a block diagram which roughly shows the constitution of said device and its way of functioning.

With reference to FIG. 2 the constitution and the function of the device according to the invention will now be described more in detail. When a person is snoring only the snoring sounds with low frequencies (in the order of 200 Hz and less) do propagate through the pillow and the bed mattress, so that these are going to act as a low-pass filter. Since the snores have typical frequencies of about 100 Hz it is advantageous to locate the device under the pillow and/or the mattress, in order to use the two latter to filter out possible sounds not emanating from snoring. The acoustic waves which reach the box 4 strikes the microphone 5 disposed therein, which transforms the sound into electrical signals. These are conducted to a high-pass filter 6 with a lower frequency limit of 80 Hz and an intensity reduction of 6 dB/octave in the direction towards lower frequencies. The signals then reach an amplifier 7 which amplifies them by 40 dB. After that they pass a filter assembly 8, which in this case consists of three bandpass filters connected in series and having a middle frequency of 100 Hz and each an intensity reduction of 12 dB/octave in both directions on the frequency scale. The signals now coming out from the filter assembly are almost without exception deriving from sounds with a frequency of 100 Hz ±20 Hz. As already mentioned this corresponds to the frequency of typical snoring sound. The signals are after this conducted to an AC/DC-converter 9, in which they are converted to direct current.

Logic means will now be described for determining if the signals passing through all the filters are periodically appearing with time intervals, which are typical for snores, in order to find out if the signals are deriving from snores.

When a logical 1-state or 0-state are discussed below, it is not necessary that there is a signal or no signal respectively, but it is also possible that a strong and a weak signal respectively are meant. For the reason of simplifying the word "logical" is omitted below.

The AC/DC-converter 9 delivers the 1-state at the output when it is reached by acoustic signals registered by the microphone and continuing at least for 0.3 seconds. The output of the AC/DC-converter is connected to a first 10 and a second 11 monostable multivibrator. The first and the second multivibrator are triggered simultaneously when a signal (corresponding to a snore) stops coming from the converter 9, so that they are delivering a 0-state at the output during approximately 5 seconds and a 1-state during approximately 1.5 seconds respectively. The period of time of the first multivibrator is after that prolonged by 5, seconds if a signal is arriving from the converter and disappears again before the first period of time expires. As long as the snoring is continous this multivibrator will never get a 1-state at the output, but if on the contrary the interruption between two snores is longer than 5, seconds a 1-state at the output will be conducted to an OR-gate 12 which in its turn delivers a 1-state at the output, which is conducted to a resetting input of a counter 13 counting the number of snores. Accordingly, the purpose of the first multivibrator is to ensure that sounds which are not returning within a predetermined period of time here 5 seconds, are not counted as (disturbing) snores.

The output of the second multivibrator 11 is fed back to the input, so that a new triggering cannot prolong the period of time (1.5 seconds) during which it delivers a 1-state at the output. The output of the second multivibrator is also as well as the output of the AC/DC-converter connected to the input of an AND-gate 14. The output of the AND-gate is in its turn connected to the input of the OR-gate 12. As a consequence of this fact, if a 1-state is delivered at the output of the converter during the first 1.5 seconds after the preceding 1-state disappeared and accordingly while the second multivibrator 11 has a 1-state at its output, the AND-gate 14 delivers the 1-state at its output and the counter 13 is reset. Accordingly, the purpose of the second multivibrator is to ensure that sounds that do not have a predetermined minimum time interval, here 1.5 seconds, before they occur again, are not counted as snores either. By this it is possible to exclude the registering of talking in sleep and possible background sounds as being snores.

The output of the second multivibrator 11 is also connected to an input of the counter 13, which counts a snore when the 1-state at the output of said multivibrator changes to a 0-state. The counter delivers after a predetermined number of counted snores, e.g. five, a 1-state at its output. This number may be externally adjusted, but it is also possible to fix it in the manufacturing of the device. Thus, when it has been recognized and settled that a sleeping person is continously snoring, the counter will deliver a 1-state at its output which is conducted to a third monostable multivibrator 15, which by this state is triggered to a 1-state at its output during a time of about 5 seconds. At the same time a signal is conducted from the output of the counter to the OR-gate, which causes the resetting of the counter. The signal from the third multivibrator 15 is led to a power unit 16 which drives an apparatus 17 adapted to influence a snoring person, so that he stops snoring. The apparatus or influencing means here of a vibrator sending out vibrations perceptible to the sleeping person which influence him to change his sleeping position without waking up. If he does still snore the vibrator 17 stops acting upon him, the cycle described above is started again, in order to start acting upon the snorer after five additional snores, preferably in such a manner that he changes to a position ending the snoring.

The arrangement for detecting snoring sounds thus comprises elements 5 through 14, the elements 10 through 14 comprising the logic means.

The device according to the invention is not at all limited to the embodiment example described above, but all kinds of modification possibilities should through the knowledge of the invention be obvious to a man skilled in the art without deviating from the scope of the invention.

The values of time periods, frequencies, and the like mentioned above can naturally be varied in an appropriate manner. It is also possible to obtain the same function as above by means of other types of circuit diagrams. The elements of the device do not necessarily have to be disposed in one and the same box, although this can be very convenient. The latter does not have to be intended to be located under the mattress either.

The apparatus 17 acting upon the snorer can for example transmit acoustic signals only registrable by that person, induce a moving of the pillow in order to change the head position of the snorer or influence the snorer in another appropriate manner to stop his disturbing activity preferably without waking him up.

It would also be possible to design the arrangement of the device so that it also measures other periodical body functions, for example heartbeats or the like, in order to deliver information intended to be used in an appropriate manner.

Finally the apparatus 17 could be arranged to wake the snoring person up if it would be necessary in order to influence him to stop snoring.

We claim:

1. A device for preventing snoring by a sleeping person, comprising:
   sound-receiving means for receiving sounds and for delivering signals when snoring sounds are received;
   logic means connected to said sound-receiving means for receiving the signals and activation pulses when said signals are determined by said logic means to be arriving periodically at time intervals which are typical of snores, said logic means including a counter means for counting the number of signals and upon counting a selected number of signals for supplying an activation pulse and influencing means connected to said counter means for receiving said activation pulses, said influencing means being activated by an activation pulse to influence a sleeping person to stop producing snoring sounds.

2. A device according to claim 1, wherein said sound-receiving means comprises a microphone for receiving sounds in combination with at least one of a mattress and a pillow disposed over said microphone and adapted for receiving a sleeping person to act as a low-pass filter for sounds received by said microphone.

3. A device according to claim 1, wherein said logic means includes a first multivibrator means connected between said sound-receiving means and said counter means for receiving the signals and for resetting said counter means if, after an initial signal, no subsequent signal is received within a selected time period.

4. The device according to claim 3, wherein said logic means includes a second multivibrator means connected between said sound-receiving means and said counter means for receiving the signals from said sound-receiving means and for resetting said counter means if, after an initial signal, a subsequent signal is received within a second selected time period which is shorter than said first-mentioned selected time period so that the counter means is reset when sounds are received by said sound-receiving means which are more frequent than the time intervals typical for snores.

5. A device according to claim 4, wherein said first and second multivibrator means each have a first input for changing the state of said multivibrator means said second multivibrator means having a second input for changing the state of said second multivibrator means, each multivibrator means having an output, said logic means including an OR-gate having a plurality of inputs and one output and an AND-gate having a plurality of inputs and one output, said output of said AND-gate being connected to one input of said OR-gate, said output of said first multivibrator means being connected to one input of said OR-gate, said AND-gate having one input connected to said sound-receiving means for receiving the signals and another input connected to said output of said second multivibrator means, said first input of each of said multivibrator means being connected to said sound-receiving means for receiving the signals, said counter means having a resetting input and a counting input, the output of said OR-gate being connected to said resetting input and the output of said second multivibrator means being connected to said counting input and in a feedback connection to said second input of said second multivibrator means, said output of said counter means being connected to one input of said OR-gate and to said influencing means for providing said activating pulses to said influencing means.

6. A device according to claim 1, wherein said influencing means comprises a generator means for delivering a time-limited, acoustic signal adapted to be only perceptible by the sleeping person.

7. A device according to claim 1, wherein said influencing means comprises a generator means for delivering a time-limited vibration action to the sleeping person.

8. A device according to claim 1, wherein said influencing means includes means for influencing the sleeping person for a selected period of time and being connected to said logic means for resetting said counter means upon expiration of said selected period of time.

9. A device according to claim 1, including a box containing said sound-receiving means, said logic means and said influencing means, said box being adapted for positioning below a sleeping person under a pillow and mattress for supporting a sleeping person.

10. The device according to claim 1, wherein said sound-receiving means comprises a microphone for receiving sounds, filter means connected to said microphone for filtering high and low frequencies from the sounds and for forming a signal from sounds within a frequency range and convertor means for converting the sounds within the frequency range into logical pulses having a first state when sounds within the frequency range are received by said convertor means and switching to a second state at other times, said logic means comprising a first multivibrator means having an input connected to said convertor means for receiving said logical pulses and an output for switching from the first state to the second state upon switching of the logical pulse from the first state to the second state, which is indicative of termination of sounds having the frequency range, said output of said first multivibrator means switching back from said second state to said first state after expiration of a first selected period of time, said logic means including a second multivibrator means having a first input connected to said convertor means for receiving said logical pulses, a second input and an output, said output of said second multivibrator means switching from the second state to the first state upon switching of said logical pulse from the first state to the second state, said output of said second multivibrator means switching back from the first state to the second state upon expiration of a second period of time which is shorter than said first period of time, the difference between said first and second periods of time being selected to be characteristic of a characteristic interval between snoring sounds, said logic means including an AND-gate having a first input connected to said convertor means for receiving said logical pulses and a second input connected to said output of said second multivibrator means and said AND-gate having an output, an OR-gate having a first input connected to said output of said first multivibrator means, a second input connected to said output of said AND-gate, said OR-gate having an third input and an output, said counter means having a resetting input connected to said output of said OR-gate and a counting input connected to said output of said second multivibrator means, said output of said second multivibrator means being connected in feedback to said second input of said second multivibrator means for resetting the state of the output of said second multivibrator means, said counter means having an output for carrying said activating pulses which are logical pulses having one of the first and second state for activating said influencing means, said output of said counter means being connected to said third input of said OR-gate for influencing said OR-gate to reset said counter.

11. A device according to claim 10, wherein said influencing means includes a third multivibrator means having an input connected to said output of said counter means, said third multivibrator means having an output, said influencing means including a power unit connected to said output of said third multivibrator means, for activation with a change of state of said third multivibrator means and an influencing mechanism connected to said power unit for influencing a sleeping person and activeable with activation of said power unit.

* * * * *